US010188369B2

(12) United States Patent
Pelissier et al.

(10) Patent No.: US 10,188,369 B2
(45) Date of Patent: Jan. 29, 2019

(54) METHODS AND APPARATUS FOR PERFORMING MULTIPLE MODES OF ULTRASOUND IMAGING USING A SINGLE ULTRASOUND TRANSDUCER

(71) Applicant: Clarius Mobile Health Corp., Burnaby (CA)

(72) Inventors: Laurent Pelissier, North Vancouver (CA); Kris Dickie, Vancouver (CA); Nishant Uniyal, Vancouver (CA)

(73) Assignee: Clarius Mobile Health Corp., Burnaby, British Columbia (CA)

( * ) Notice: Subject to any disclaimer, the term of this patent is extended or adjusted under 35 U.S.C. 154(b) by 318 days.

(21) Appl. No.: 15/207,203

(22) Filed: Jul. 11, 2016

(65) Prior Publication Data
US 2018/0008233 A1    Jan. 11, 2018

(51) Int. Cl.
*A61B 8/14*     (2006.01)
*A61B 8/00*     (2006.01)
*G01S 7/52*     (2006.01)
*A61B 8/08*     (2006.01)
*G01S 15/89*    (2006.01)

(52) U.S. Cl.
CPC .......... *A61B 8/4494* (2013.01); *A61B 8/4488* (2013.01); *A61B 8/5207* (2013.01); *G01S 7/52046* (2013.01); *G01S 7/52085* (2013.01); *G01S 7/52098* (2013.01); *G01S 15/892* (2013.01); *G01S 15/8918* (2013.01); *G01S 15/8927* (2013.01)

(58) Field of Classification Search
CPC ....................................................... A61B 8/00
See application file for complete search history.

(56) References Cited

U.S. PATENT DOCUMENTS

| 4,409,982 | A | * | 10/1983 | Plesset | ............... | G01N 29/0609 |
| | | | | | | 600/447 |
| 5,269,309 | A | * | 12/1993 | Fort | ........................ | G01H 5/00 |
| | | | | | | 600/447 |
| 7,115,093 | B2 | | 10/2006 | Almann et al. | | |

(Continued)

OTHER PUBLICATIONS

Bjorn A.J. Angelsen, Hans Torp, Sverre Holm, Kjell Kristoffersen, and T.A. Whittingham, "Which transducer array is best?", European Journal of Ultrasound, Mar. 1995, 2 (1995) 151-164.

(Continued)

*Primary Examiner* — Joel F Brutus
(74) *Attorney, Agent, or Firm* — Julian Ho

(57) ABSTRACT

The present embodiments relate generally to ultrasound imaging methods and apparatus that allow for multiple modes of imaging using a single ultrasound transducer having a plurality of transducer elements. In an embodiment, there is provided an ultrasound imaging machine that is: operable in a first imaging mode in which the plurality of transducer elements are activated; and operable in a second imaging mode different from the first imaging mode, and in the second imaging mode, a subset of the plurality of transducer elements are activated so that ultrasound signals are steered from the subset of the plurality of transducer elements, where any remaining transducer elements of the plurality of transducer elements not part of the subset are inactive when operating in the second imaging mode.

18 Claims, 6 Drawing Sheets

(56) References Cited

U.S. PATENT DOCUMENTS

| | | | |
|---|---|---|---|
| 8,118,747 B2 | 2/2012 | Uria et al. | |
| 8,535,227 B2 | 9/2013 | Almann et al. | |
| D724,745 S | 3/2015 | Drome et al. | |
| 2006/0058672 A1* | 3/2006 | Klepper | B06B 1/0622 600/447 |
| 2009/0105592 A1* | 4/2009 | Yao | A61B 8/0883 600/447 |
| 2009/0112091 A1* | 4/2009 | Chiang | A61B 8/463 600/447 |
| 2010/0137716 A1 | 6/2010 | Liu et al. | |
| 2010/0249598 A1 | 9/2010 | Smith et al. | |
| 2011/0224552 A1 | 9/2011 | Poland et al. | |
| 2014/0243669 A1 | 8/2014 | Halmann et al. | |
| 2015/0343492 A1* | 12/2015 | Hajati | B06B 1/0622 73/661 |

OTHER PUBLICATIONS

Thomas L. Szabo and Peter A. Lewin, "Ultrasound Transducer Selection in Clinical Imaging Practice", Journal of Ultrasound in Medicine, Apr. 1, 2013, vol. 32, No. 4, 573-582.

Eberhard Brunner, "How Ultrasound System Considerations Influence Front-End Component Choice", Analog Dialogue, May-Jul. 2002, vol. 36, No. 3.

Pattarin Pirompanich, "Basic Principles of Ultrasound and Technique", slide deck published Sep. 4, 2015, available at http://www.slideshare.net/pattarin/basic-principles-of-lung-ultrasound, last accessed Jul. 27, 2016.

Franco Vallejos, "Ultrasound Physics—Transducer Arrays", video published Jul. 6, 2013 by Exam Refresh, available at https://www.youtube.com/watch?v=AG2ITLh1eUo, last accessed Jul. 28, 2016.

"Sound Beam and Resolution", Sonography Folder, publication date unknown, webpage available at https://sites.google.com/site/sonographyfolder/ultrasound-physics/sound-beam-and-resolution, last accessed Jul. 28, 2016.

Frank Miele, "Quick Concepts: Grating Lobes", Pegasus Lectures Inc., published Jan. 28, 2015, webpage available at https://www.pegasuslectures.com/blog/2015/01/28/quick-concepts-grating-lobes/, last accessed Jul. 28, 2016.

"Intro To Ultrasonic testing", Olympus, publication date unknown, webpage available at http://www.olympus-ims.com/en/ndt-tutorials/intro/ut/, last accessed Jul. 28, 2016.

"Vscan with Dual Probe", GE Healthcare, publication date unknown, webpage available at http://www3.gehealthcare.com/en/products/categories/ultrasound/vscan_portfolio/vscan_with_dual_probe, last accessed Jul. 28, 2016.

Abstract of J. Ylitalo, "Synthetic aperture ultrasound imaging using a convex array", Ultrasonics Symposium, 1995 Proceedings, 1995 IEEE (vol. 2), Date of Conference: Nov. 7-10, 1995.

* cited by examiner

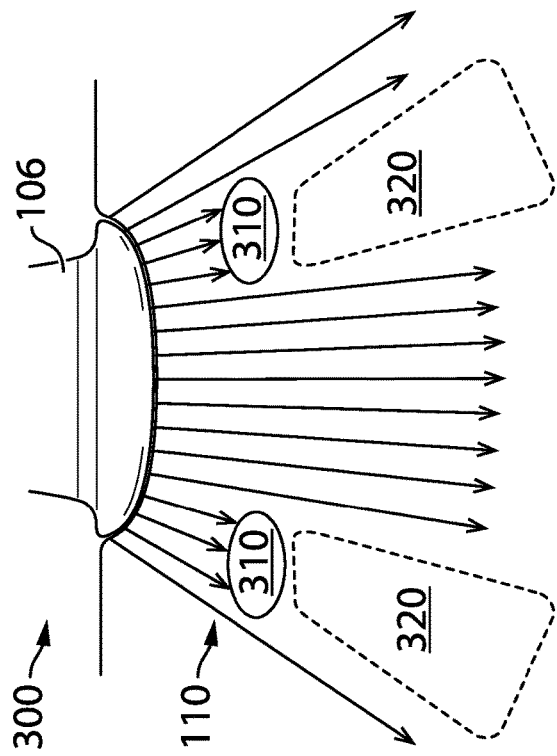
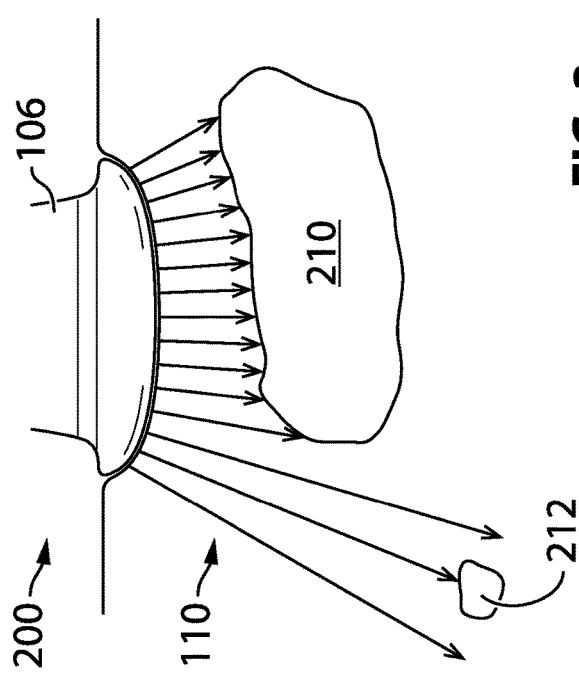
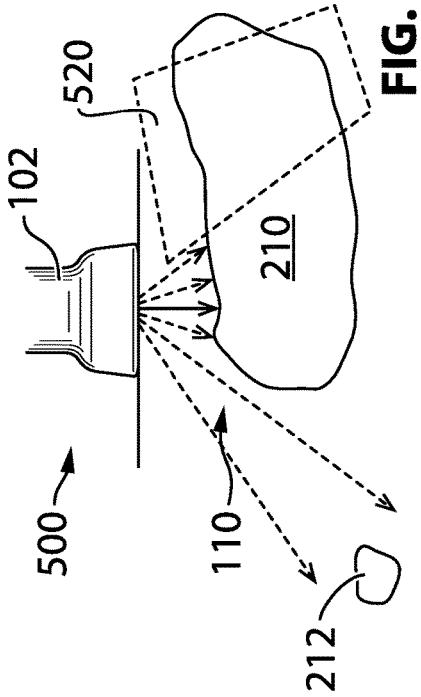
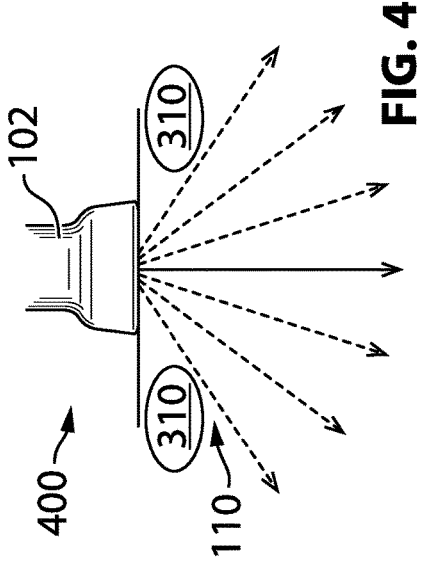

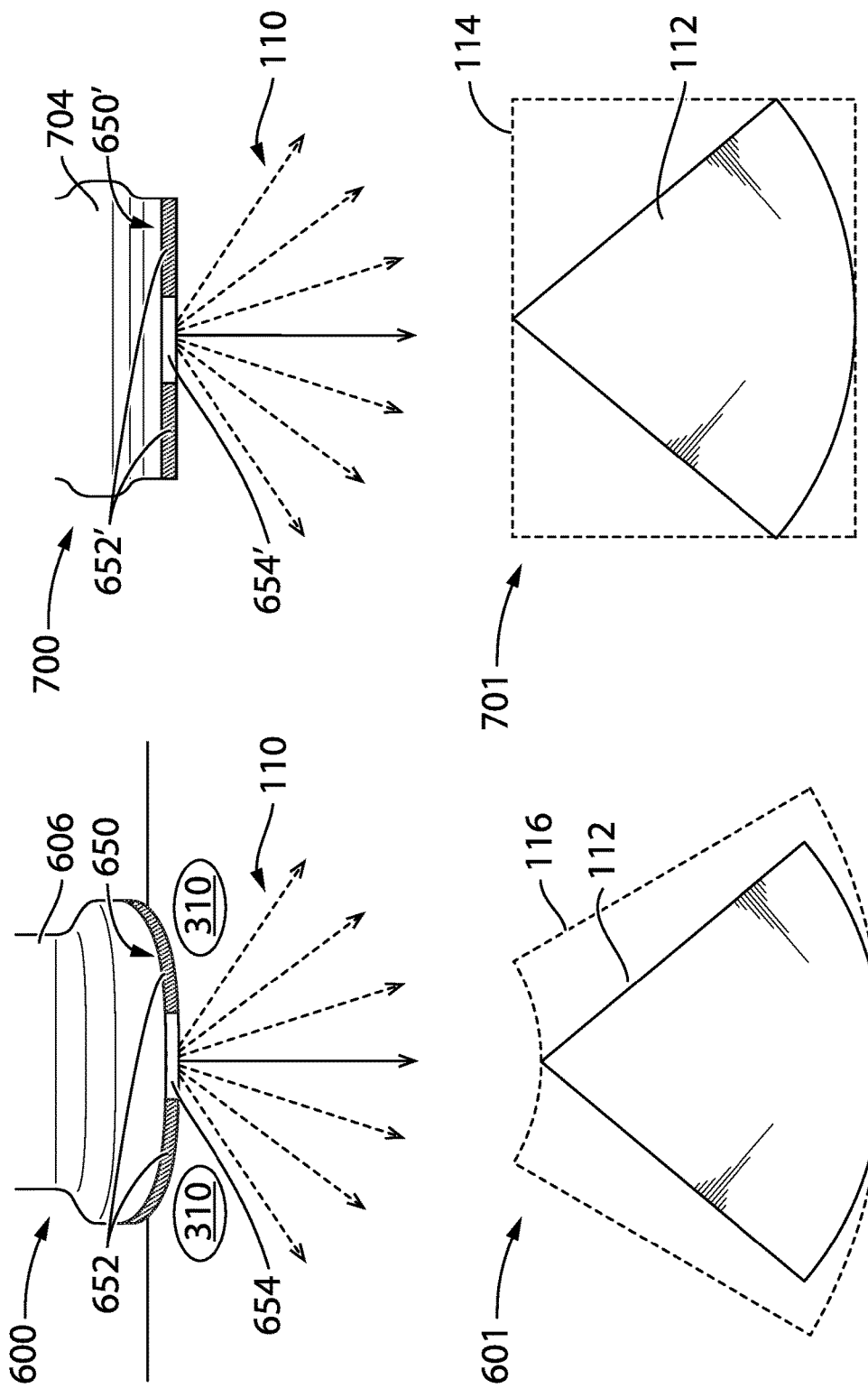

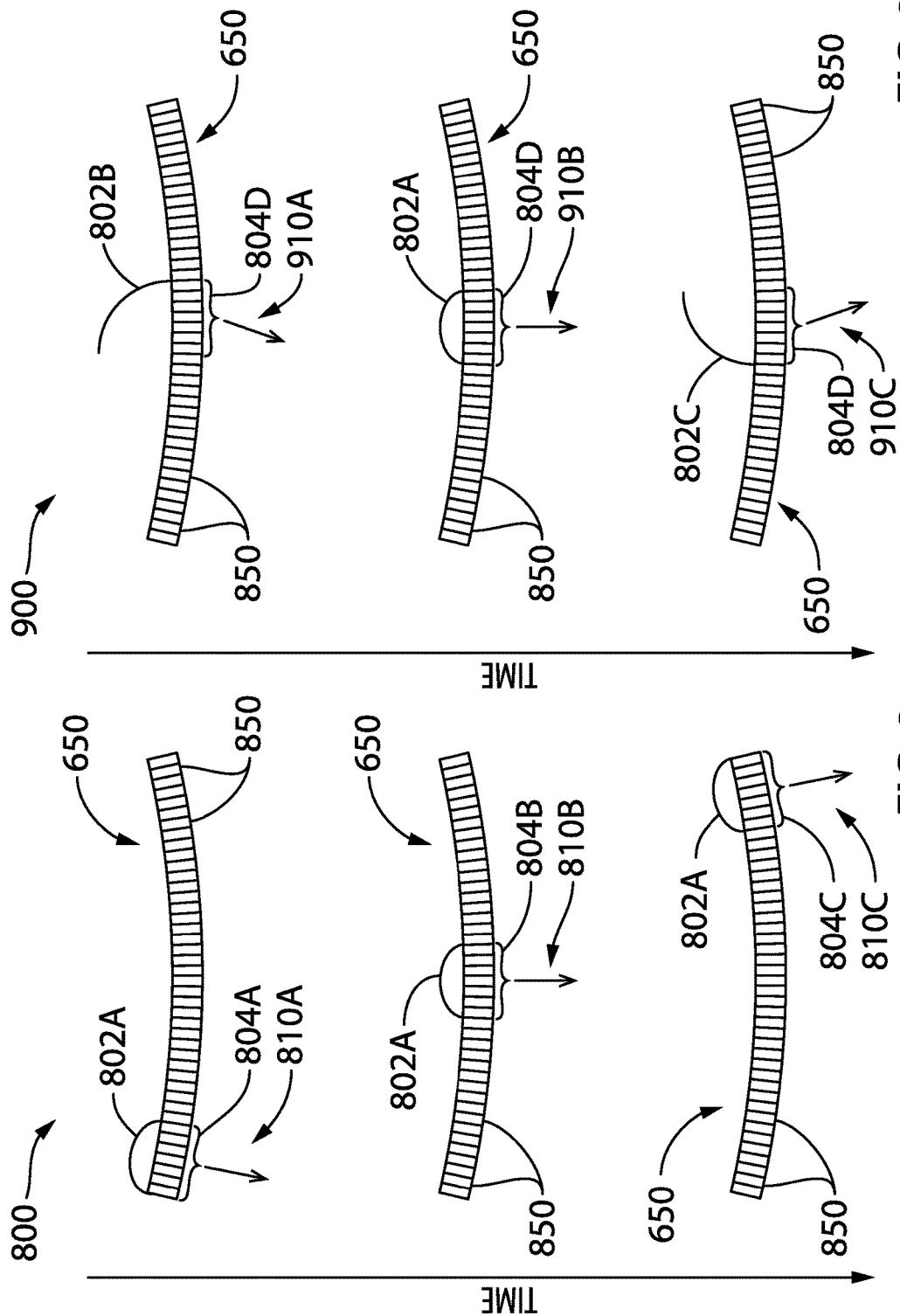

METHODS AND APPARATUS FOR PERFORMING MULTIPLE MODES OF ULTRASOUND IMAGING USING A SINGLE ULTRASOUND TRANSDUCER

FIELD

The present disclosure relates generally to ultrasound imaging, and in particular, methods and apparatus that enable multiple modes of ultrasound imaging using a single ultrasound transducer.

BACKGROUND

Ultrasound imaging has a wide range of medical applications. For example, ultrasound imaging provides a relatively fast and non-invasive way to assess abdominal organs such as the bladder, liver, uterus, kidneys, and the like. Ultrasound imaging may also be used to obtain images of the heart.

Traditional ultrasound systems are typically used with a number of different ultrasound probes that are designed to image different parts of the body. Ultrasound probes (also called ultrasound transducers) generally contain a number of transducer elements that can be selectively pulsed to generated ultrasound signals. These ultrasound signals are projected into a volume of tissue and corresponding echo signals are processed to generate an ultrasound image. Different types of ultrasound probes have different transducer element configurations to allow for imaging different parts of the body.

For example, a phased-array probe typically has a small footprint containing a small number of transducer elements positioned on the probe head. The small footprint allows the probe to be positioned on parts of the body that have constricted space. To obtain a sufficiently wide field of view using the small number of transducer elements on the probe head, the ultrasound signals are steered in many different directions during multiple phases when projected into the volume of tissue being imaged. The phased multi-directional steering of a phased-array probe makes it suitable for imaging the heart because the ultrasound signals can be projected through the intercostal space in between a patient's ribs.

In another example, a sequential curvilinear-array probe (also called a convex or curved probe) contains a larger footprint with a higher number of transducer elements on the probe head. The higher number of transducer elements allow for ultrasound signals to be sequentially projected from different portions of a larger surface area on the probe head, so that an ultrasound image can be obtained without the ultrasound signals having to be steered in many different directions to obtain a desired field of view. As compared with a phased-array probe, use of a sequential curvilinear-array probe with a higher number of transducer elements can allow a larger volume of tissue to be imaged. Where there are no constricted spaces or anatomical structures (e.g., ribs) that would make it difficult to image a particular organ, ultrasound operators may generally prefer to use a probe with a larger surface area so as to obtain the widest field of view. For example, sequential curvilinear-array probes are conventionally used to image the abdomen.

When examining a patient, an ultrasound operator may need to switch probes during the examination in order to complete the examination (e.g., to examine the heart with a phased-array probe, and the abdomen with a sequential curvilinear-array probe). Switching probes typically involves physically removing one probe from an ultrasound machine, plugging in a different probe, and operating one or more controls on the ultrasound machine to cause the ultrasound machine to operate in the desired imaging mode that works with the newly-attached probe. This can be time consuming, and can present problems in certain medical environments such as critical emergency care.

Additionally, it is generally desirable to cover a probe with a sterile cover to protect patients from contamination. This step of adding a sterile cover increases the time needed to change probes and may further delay an examination.

There is a need for improved methods and apparatus for imaging different areas of a patient without the need to switch between different probes.

BRIEF DESCRIPTION OF THE DRAWINGS

Non-limiting examples of various embodiments of the present disclosure will next be described in relation to the drawings, in which:

FIG. 2 shows a sequential curvilinear-array transducer operating in a conventional manner to perform imaging;

FIG. 3 shows at least some limitations of a sequential curvilinear-array transducer operating in a conventional manner;

FIG. 4 shows a phased-array transducer operating in a conventional manner to perform imaging;

FIG. 5 shows at least some limitations of a phased-array transducer operating in a conventional manner;

FIG. 6 shows a multi-mode curvilinear-array transducer configured to perform imaging in a manner similar to a phased-array transducer, in accordance with at least one embodiment of the present invention;

FIG. 7 shows a multi-mode linear-array transducer configured to perform imaging in a manner similar a phased-array transducer, in accordance with at least one embodiment of the present invention;

FIG. 8 shows the time delays and apertures used to perform beamforming when a multi-mode curvilinear-array transducer is operated in the first imaging mode, in accordance with at least one embodiment of the present invention;

FIG. 9 shows the time delays and apertures used to perform beamforming when a multi-mode curvilinear-array transducer is configured to perform imaging in the second imaging mode, in accordance with at least one embodiment of the present invention;

DETAILED DESCRIPTION

Figure 1:
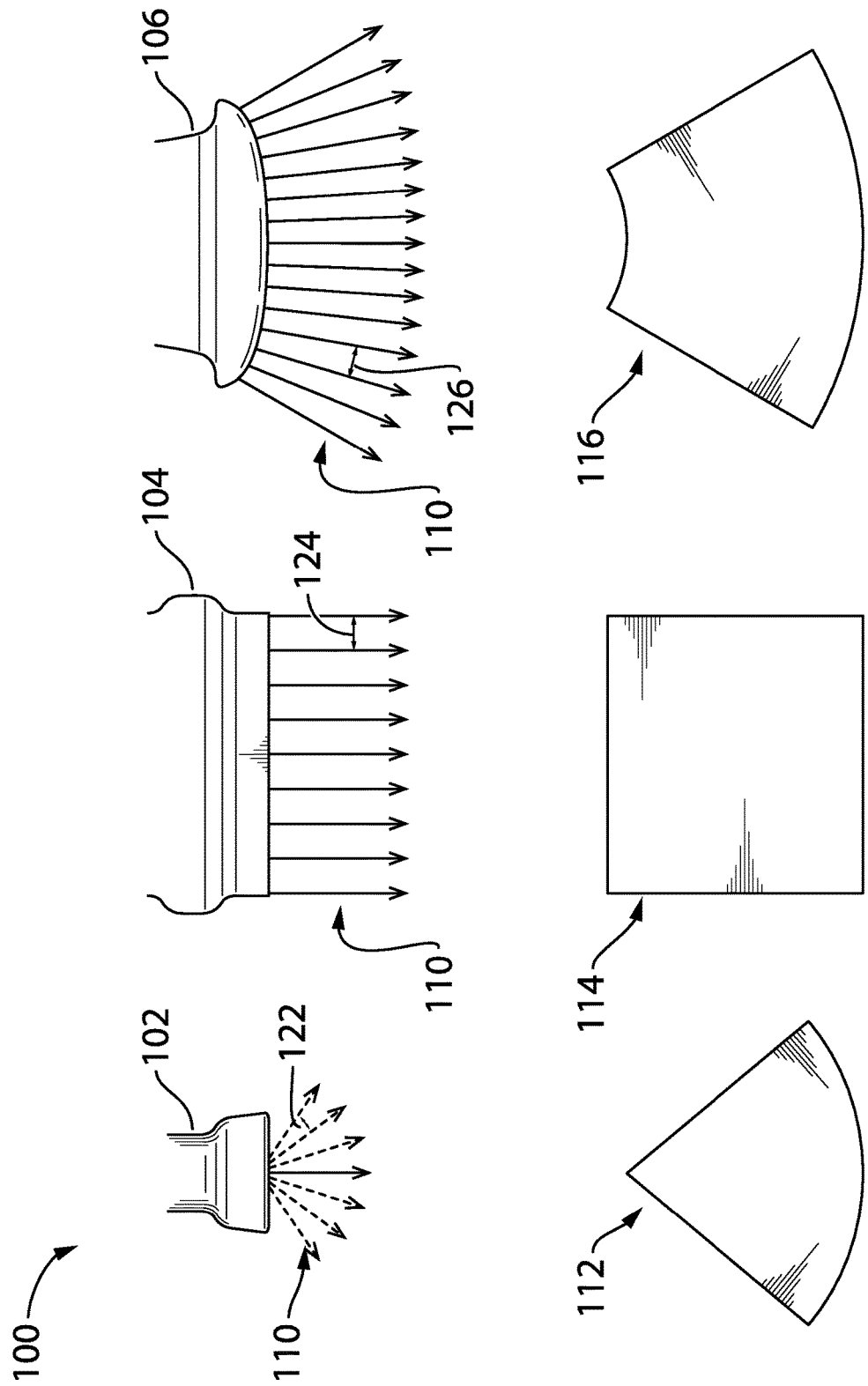
FIG. 1 shows a number of example traditional ultrasound transducer types and the corresponding generated images.

In a first broad aspect of the present disclosure, there is provided an ultrasound imaging method that involves an ultrasound imaging machine: imaging in a first mode using a sequential transducer including a plurality of transducer elements, wherein when imaging in the first mode, the plurality of transducer elements are activated; and imaging in a second mode different from the first mode, wherein when imaging in the second mode, a subset of the plurality of transducer elements are activated and a plurality of ultrasound signals are steered from the subset of the plurality of transducer elements, and wherein any remaining transducer elements of the plurality of transducer elements not part of the subset are inactive when imaging in the second mode.

In some embodiments, the imaging in the first mode further includes pulsing groups of adjacent transducer elements of the plurality of transducer elements in a sequential manner, and the imaging in the second mode further includes pulsing the subset of the plurality of transducer elements in a phased manner to generate the plurality of ultrasound signals.

In some embodiments, when imaging in the first mode, the pulsing of the groups of adjacent transducer elements is performed for the purpose of beamforming, and the groups of adjacent transducer elements correspond to respective different apertures along a head of the sequential transducer. In some embodiments, when imaging in the second mode, the pulsing of the subset of the plurality of transducer elements in a phased manner is performed for the purpose of beamforming through a single aperture on the head of the sequential transducer.

In some embodiments, the beamforming performed when imaging in the first mode includes delayed activation of the transducer elements within each of the groups of adjacent transducer elements, and a same time delay is used for all the groups of adjacent transducer elements corresponding to the respective different apertures along the head of the sequential transducer. In some embodiments, the beamforming performed when imaging in the second mode includes delayed activation of the transducer elements within the subset of transducer elements, and the beamforming is repeatedly performed on the subset of transducer elements using a plurality of different time delays to steer the plurality of ultrasound signals from the single aperture on the head of the sequential transducer.

In some embodiments, when imaging in the second mode, each of the plurality of ultrasound signals is steered in a respective different direction so that a sector image is generated. In some embodiments, the sector image has a sector angle of 60 to 90 degrees. In some embodiments, angular spacing between the respective different directions is between 0.35 to 0.70 degrees.

In some embodiments, the sequential transducer is a curvilinear-array transducer, and the plurality of transducer elements are arranged along an arc having a radius of curvature. In some embodiments, the radius of curvature is between 30 to 120 millimeters.

In some embodiments, the sequential transducer is a linear-array transducer, and the plurality of transducer elements are arranged in a line.

In some embodiments, the plurality of transducer elements have a pitch spacing between each adjacent transducer element, and the pitch spacing is between 100 to 400 microns.

In some embodiments, the plurality of transducer elements have at least 128 transducer elements and the subset of the plurality of transducer elements include 16 to 96 of the at least 128 transducer elements.

In some embodiments, the ultrasound imaging machine is provided in a form factor that has a mass less than 4.5 kilograms.

In another broad aspect of the present disclosure, there is provided an ultrasound imaging machine including: an ultrasound processor; and a sequential transducer communicably coupled to the ultrasound processor, the sequential transducer including a plurality of transducer elements. The ultrasound imaging machine is: operable in a first imaging mode in which the ultrasound processor activates the plurality of transducer elements; and operable in a second imaging mode different from the first imaging mode, and in the second imaging mode, the ultrasound processor activates a subset of the plurality of transducer elements so that a plurality of ultrasound signals are steered from the subset of the plurality of transducer elements, wherein any remaining transducer elements of the plurality of transducer elements not part of the subset are inactive when operating in the second imaging mode.

In some embodiments, when operating in the first imaging mode, the ultrasound processor is configured to pulse groups of adjacent transducer elements of the plurality of transducer elements in a sequential manner, and when operating in the second imaging mode, the ultrasound processor is further configured to pulse the subset of the plurality of transducer elements in a phased manner to generate the plurality of ultrasound signals.

In some embodiments, when operating in the first imaging mode, the pulsing of the groups of adjacent transducer elements is performed for the purpose of beamforming, and the groups of adjacent transducer elements correspond to respective different apertures along a head of the sequential transducer. In some embodiments, when operating in the second imaging mode, the pulsing of the subset of the plurality of transducer elements in a phased manner is performed for the purpose of beamforming through a single aperture on the head of the sequential transducer.

In some embodiments, the beamforming performed when in the first imaging mode includes delayed activation of the transducer elements within each of the groups of adjacent transducer elements, and a same time delay is used for all the groups of adjacent transducer elements corresponding to the respective different apertures along the head of the sequential transducer. In some embodiments, the beamforming performed when in the second imaging mode includes delayed activation of the transducer elements within the subset of transducer elements, and the beamforming is repeatedly performed on the subset of transducer elements using a plurality of different time delays to steer the plurality of ultrasound signals from the single aperture on the head of the sequential transducer.

In some embodiments, each of the plurality of ultrasound signals is steered in a respective different direction, so that a sector image is generated. In some embodiments, the sector image has a sector angle of 60 to 90 degrees. In some embodiments, angular spacing between the respective different directions is between 0.35 to 0.70 degrees.

In some embodiments, the sequential transducer includes a curvilinear transducer, and the plurality of transducer elements are arranged along an arc having a radius of curvature. In some embodiments, the radius of curvature is between 30 to 120 millimeters.

In some embodiments, the sequential transducer is a linear-array transducer, and the plurality of transducer elements are arranged in a line.

In some embodiments, the plurality of transducer elements have a pitch spacing between each adjacent transducer element, and the pitch spacing is between 100 to 400 microns.

In some embodiments, the plurality of transducer elements includes at least 128 transducer elements and the subset of the plurality of transducer elements includes 16 to 96 of the at least 128 transducer elements.

In some embodiments, the sequential transducer includes a housing containing the plurality of transducer elements, and the housing includes a marking indicating a position of the subset of the plurality of transducer elements amongst the plurality of transducer elements.

In some embodiments, the ultrasound imaging machine is provided in a form factor that has a mass less than 4.5 kilograms.

In another broad aspect of the present disclosure, there is provided a sequential ultrasound transducer, capable of being communicably coupled to an ultrasound processor. The sequential ultrasound transducer includes: a plurality of transducer elements, wherein when the sequential ultrasound transducer is communicably coupled to the ultrasound processor, the ultrasound processor is configured to: activate the plurality of transducer elements in a first imaging mode; and activate a subset of the plurality of transducer elements in a second imaging mode that is different from the first imaging mode, wherein in the second imaging mode, the ultrasound processor steers a plurality of ultrasound signals from the subset of the plurality of transducer elements, and wherein any remaining transducer elements of the plurality of transducer elements not part of the subset are inactive, when in the second imaging mode.

In another broad aspect of the present disclosure, there is provided a multi-mode ultrasound imaging machine that has different operational modes which permit using the same ultrasound probe having the same transducer element array for multiple purposes. In one embodiment, the same transducer is used in both a steered imaging mode and a non-steered imaging mode. The non-steered imaging mode may be used, for example, to image abdominal organs. The steered imaging mode may be used, for example, to image a heart.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 are a number of example traditional ultrasound transducer types and the corresponding generated image types. As illustrated, a phased-array transducer 102, a sequential linear-array transducer 104, and a sequential curvilinear-array transducer 106 are shown. Their respective corresponding image types 112, 114, 116 are also shown.

A phased-array transducer 102 traditionally has a transducer head with a small footprint having a small number of transducer elements positioned thereon. Due to the limited number of transducer elements, the ultrasound signals 110 are projected in a phased manner in multiple directions to obtain a broader field of view. This results in a fan-shape sector image 112 being generated.

A sequential linear-array transducer 104 has a transducer head with a larger footprint on which a larger number of transducer elements are positioned in a line. Using the larger number of transducer elements, beamforming is performed on successive groups of adjacent transducer elements to direct ultrasound signals 110 into a volume of tissue being imaged. The ultrasound signals 110 are projected in a single direction orthogonal to the surface of the transducer head. Each projected ultrasound signal 110 forms a scanline, so that the cumulative scanlines form a rectangular ultrasound image 114.

A sequential curvilinear-array transducer 106 is similar to a sequential linear-array transducer 106 in that the transducer head has a larger footprint with a larger number of transducer elements than a phased-array transducer 102. However, instead of the transducer elements being positioned along a straight line, they are positioned along a curved arc. The ultrasound signals 110 directed from the transducer elements are projected in the same manner as in the sequential linear-array transducer (e.g., in a single direction orthogonal to the surface of the transducer). The placement of the transducer elements along the arc allows for a wider field of view, as is shown by the corresponding generated image type 116.

The image type 116 will have curved portions at both its top and bottom edges. In contrast, while the sector image type 112 generated by the phased-array transducer 102 also has a curved portion at its bottom edge, it's upper edge is a single point because the ultrasound signals 110 originate from a single location on the transducer head of the phased-array transducer 102.

The nature of how each transducer type operates may impact the quality of the image being acquired. For example, referring still to FIG. 1, because the phased-array transducer 102 directs ultrasound signals 110 in multiple directions from a small number of transducer elements, the distance 122 between each scanline increases as the distance from the transducer head increases. This may reduce the lateral resolution in the far field of the sector image 122 generated (e.g., the ability to resolve between two adjacent objects in a direction perpendicular to the direction of beam travel, but in-plane with the ultrasound imaging being generated).

In contrast, since the sequential linear-array transducer 104 projects parallel ultrasound signals 110 from multiple locations on the transducer head, there is a consistent distance 124 between adjacent ultrasound signals 110 in both the near field and the far field of the generated rectangular image 114. As a result, images generated using the sequential linear-array transducer 104 may not suffer from the degradation in lateral resolution present in sector images 112.

A sequential curved transducer 106 projects ultrasound signals 110 in multiple diverging directions from its curved transducer head. However, because the ultrasound signals 110 originate from multiple spots along a curved larger transducer head than the phased-array transducer 102, the distance 126 between adjacent scanlines to not diverge as significantly. As a result, the sequential curved transducer 106 has better lateral resolution in the far field than the phased-array transducer 102.

Transducer elements that operate at a high frequency (e.g., 5-12 MHz) provide better axial resolution (e.g., ability to resolve between two adjacent objects along the axis of the ultrasound signal's 110 direction of travel) than transducer elements that operate at a low frequency (e.g., 1-4 MHz). High-frequency ultrasound signals 110, however, are not able to penetrate as deep into the body as lower-frequency ultrasound signals. As a result, high-frequency transducers are typically used to image tissue close to the surface of the skin (e.g., blood vessels), and lower-frequency ultrasound signals 110 are typically used to image internal organs.

A phased-array transducer 102 is typically provided with transducer elements that operate at a relatively lower frequency (e.g., 1.5-4 MHz). For example, this allows the phased-array transducer 102 to be used to image the heart. A sequential curved transducer 106 may operate in a similar frequency range (e.g., 2-5 MHz), so as to allow the sequential curvilinear-array transducer 106 to be used for imaging abdominal organs such as the bladder, liver, uterus, kidneys, and the like.

In contrast, a sequential linear-array transducer 104 may conventionally be provided with transducer elements that operate at a higher frequency (e.g., 5-12 MHz), as such types of transducers 104 are typically used in vascular contexts where the enhanced axial resolution helps resolve blood vessels near the surface of the skin. The enhanced axial resolution of a sequential linear-array transducer 104 may also make it suitable to be used for other medical procedures near the surface of the skin (e.g., needle guidance).

Table 1 is a chart summarizing characteristics of the example transducer types shown in FIG. 1:

|  | Phased-Array Transducer 102 | Sequential Linear-Array Transducer 104 | Sequential Curvilinear-Array Transducer 106 |
| --- | --- | --- | --- |
| Transducer Head Size | Small | Large | Large |
| Frequency (MHz) | 1.5-4 | 5-12 | 2-5 |
| Penetration | Good | Poor | Good |
| Axial Resolution | Average | Very Good | Average |
| Far Field Lateral Resolution | Poor | Good | Average |
| Medical Applications | Cardiac, Lung | Vascular | Abdomen |

Conventionally, a single transducer type is associated with a single mode of operation. There is also a one-to-one mapping between transducer types 102, 104, 106 and corresponding image types 112, 114, 116. An ultrasound operator may typically select an appropriate transducer type 102, 104, 106 based on how a combination of the characteristics of a given transducer type 102, 104, 106 match the desired medical application.

For example, as noted, it may be preferred to use a sequential curvilinear-array transducer 106 to image organs within the abdomen because it provides the largest surface area of transducer head, deep penetration, and acceptable far field lateral resolution. In another example, a phased-array transducer 102 may be used to image the heart or lungs because even though there is poor far field lateral resolution, its small transducer head footprint results in phased multi-directional ultrasound signal 110 projection that allows for imaging through the intercostal space in between a patient's ribs.

As noted, switching between different ultrasound probes during an examination may be inefficient and cumbersome for an ultrasound practitioner. However, as discussed below in relation to FIGS. 2-5, using a single one of the above-noted transducer types to image an area of the body where another transducer type would be more suitable has drawbacks. For example, FIGS. 2-5 compare operation of the phased-array transducer 102 and the sequential curvilinear-array transducer 106. Although both transducers 102, 106 are configured with similar operating frequencies and can image at similar tissue depths, there are nevertheless drawbacks when any one of the two transducers are used in scenarios where the other transducer type is more appropriate.

Referring to FIG. 2, shown there generally as 200 is a sequential curved transducer operating in a conventional manner to perform imaging. As illustrated, the sequential curvilinear-array transducer 106 projects ultrasound signals 110 into the abdomen. Within the abdomen, there may be a large organ 210 and a small structure 212 that are within the field of view of the sequential curved transducer 106. As shown, due to the wide field of view in both the near field and the far field, a significant portion of the large organ 210 may be imaged. At the same time, the average far field resolution of the sequential curved transducer 106 may allow the small structure 212 to also be identified.

Referring to FIG. 3, shown there generally as 300 are at least some limitations of a sequential curved transducer operating in a conventional manner. FIG. 3 illustrates the sequential curvilinear-array transducer 106 being applied on an area of a patient's torso where there are ribs 310 and it is desired to image the organs underneath (e.g., the heart or lungs). The ribs 310, being much denser than the surrounding tissues, reflect ultrasound signals strongly. Since the sequential curved ultrasound transducer 106 is configured to project ultrasound signals 110 in a direction orthogonal to the surface of the transducer head, a number of the ultrasound signals 110 are blocked by the ribs 310. This creates volumes 320 underneath the ribs 310 that cannot be clearly imaged. Thus, a sequential curvilinear transducer 106 operated in a conventional manner can generally not acquire good images of the heart or lungs.

Referring to FIG. 4, shown there generally as 400 is a phased-array transducer operating in a conventional manner to perform imaging. Due to the small footprint of the phased-array transducer 102, the ultrasound signals 110 are projected in a variety of different directions through the space between a patient's ribs 310, so as to allow for imaging of organs thereunder. As compared to use of a sequential curvilinear-array transducer 106 to image the same part of the body (as shown in FIG. 3), it can be seen that use of a phased-array transducer 102 allows for imaging of volumes that would otherwise be difficult to image.

Referring to FIG. 5, shown there generally as 500 are at least some limitations of a phased-array transducer operating in a conventional manner. While it may seem that the phased-array transducer 102 can be used for general-purpose imaging, there are also drawbacks to using the phased-array transducer 102 where a sequential curvilinear-array transducer 106 is more appropriate. FIG. 5 shows use of a phased-array transducer 102 to image the same volume of the abdomen as was shown in FIG. 2. The volume contains a large organ 210 and a small structure 212.

Although the phased-array transducer 102 may be able to image portions of the large organ 210, it can be seen that there are volumes 520 (shown in dotted outline) imaged by the curvilinear-array transducer 106 that are missed by the phased-array transducer 102. This may result in the phased-array transducer 102 not being able to image the large organ 210 effectively.

At the same time, due to the poor far field lateral resolution of the phased-array transducer 102, it is possible that imaging using the phased-array transducer 102 may result in the scanlines completely failing to identify the small structure 212 in the far field. These are at least two reasons why a traditional phased-array transducer 102 may perform poorly when imaging in scenarios where a sequential curvilinear-array transducer 106 would be more appropriate.

In view of the foregoing, it is apparent that any single existing traditional transducer type discussed in FIG. 1 may not be able to image multiple areas of a patient's torso. However, requiring an ultrasound operator to switch between multiple transducer types is also cumbersome and may be undesirable.

Some existing attempts to address these drawbacks include a dual-headed probe that allows for different types of scanning from different ends of the same probe (e.g., as is available with a product called Vscan with Dual Probe™ available from GE Healthcare™). Other existing attempts include configurations with a single probe having interchangeable heads, such that different transducer geometries can be used with the same handle. However, these attempts still require different heads to be used for different types of scanning. The present embodiments may alleviate at least some of the discussed drawbacks in an improved way.

Referring to FIG. 6, shown there generally as 600 is a multi-mode curvilinear-array transducer configured to perform imaging in a manner similar to a phased-array transducer, in accordance with at least one embodiment of the present invention. In the present embodiments, a multi-mode curvilinear-array transducer 606 is configured to operate in at least two modes. In the first mode, the multi-mode curvilinear-array transducer 606 operates in the conventional manner. As discussed above in relation to FIGS. 1 and 2, during operation in this first mode, scanlines (not shown in FIG. 6) may be successively and sequentially generated by pulsing groups of adjacent transducer elements present on the transducer head 650. These scanlines are created by directing the ultrasound signals 110 in a direction orthogonal to the surface of the transducer head 650. While all of the transducer elements on the transducer head 650 are typically activated when imaging in the first mode, in some embodiments, less than all of the transducer elements on the transducer head 650 may be activated in the first mode.

In the second mode, the multi-mode curvilinear-array transducer 606 activates only a subset 654 of the transducer elements that were activated in the first imaging mode. At the same time, the ultrasound signals 110 projected from this subset 654 of transducer elements are steered. For example, this may involve the transducer elements in the subset 654 being pulsed in a phased manner to generate a number of ultrasound signals 110 from the same portion of the transducer head 650. In some embodiments, the steering of the ultrasound signals 110 may be in different directions so that a sector image 112 (as shown in FIG. 1) is generated.

During operation in the second mode, any remaining transducer elements 652 not in the subset 654 remain inactive. This is so even if those transducer elements would normally be pulsed during the image acquisition process when a sequential curvilinear-array transducer 106 (as shown in FIGS. 1-3) is used in a conventional manner.

By providing a curvilinear-array transducer 606 with a second mode of operation that activates only a subset 654 of the available transducer elements and simultaneously steers the ultrasound signals 110 generated from the subset 654 of transducer elements, the multi-mode curvilinear-array transducer 606 may be able to simulate operation of a phased-array transducer 102 (as shown in FIGS. 1, 4, 5). This may allow the multi-mode curvilinear-array transducer 606 to image volumes of tissue that would otherwise not be viewable using a conventional sequential curvilinear-array transducer 106.

Shown generally as 600 in FIG. 6, when operated in the second mode, the multi-mode curvilinear-array transducer 606 is able to project ultrasound signals 110 in between the space between ribs 310 to image organs such as the heart and lungs. This allows ultrasound operators to use a single transducer to image in situations that typically require multiple transducers (e.g., a conventional sequential curvilinear-array transducer 106 and a conventional phased-array transducer 102). The multiple modes of operation may alleviate some of the drawbacks associated with having to switch transducer probes. For example, use of a single multi-mode curvilinear-array transducer 606 in situations that traditionally require multiple transducers may allow for expedited examinations during time-sensitive medical applications such as emergency care (e.g., when performing a Focused Assessment with Sonography for Trauma, or FAST, examination to assess a patient for internal bleeding and/or other trauma-related effects).

Shown generally as 601 in FIG. 6 are the image types 112, 116 that can be obtained using the multi-mode curvilinear-array transducer 606. As shown, both the conventional field of view image type 116 and a sector image type 112 can be obtained using a single multi-mode curvilinear-array transducer 606. Referring briefly to FIG. 1, this contrasts with the conventional one-to-one mapping between transducer types 102, 104, 106 and image types 112, 114, 116.

Referring to FIG. 7, shown there generally as 700 is a multi-mode linear-array transducer configured to perform imaging in a manner similar to a phased-array transducer, in accordance with at least one embodiment of the present invention. As noted above, a conventional sequential linear-array transducer 104 (as shown in FIG. 1) is typically configured with transducer elements that operate at a high frequency to provide better axial resolution in the near field. In some embodiments of the present disclosure, there is provided a multi-mode linear-array transducer 704 that is provided with transducers elements that emit ultrasound signals at the same high frequency range that is typically emitted by conventional sequential linear-array transducers 104. Similar to the multi-mode curvilinear-array transducer 606 discussed above in relation to FIG. 6, the multi-mode linear-array transducer 704 may also be configured to operate in at least two modes.

In the first mode, the multi-mode linear-array transducer 704 operates in a manner similar to the conventional operation of a sequential linear-array transducer 104. As discussed above in relation to FIG. 1, during operation in this first mode, scanlines may be successively and sequentially generated by pulsing groups of adjacent transducer elements present on the transducer head 650'. These scanlines (not shown in FIG. 7) are created by directing the ultrasound signals 110 in a direction orthogonal to the linear surface of the transducer head 650'. As was the case with the multi-mode curvilinear-array transducer 606 of FIG. 6, it may be possible that all of the transducer elements on the transducer head 650' are activated when imaging in the first mode. However, in some embodiments, less than all of the transducer elements on the transducer head 650' may be activated in the first mode.

The multi-mode linear-array transducer 704 may be configured to have a second mode of operation that is similar to the second mode of operation of the multi-mode curvilinear-array transducer 606 discussed in relation to FIG. 6. For example, referring still to FIG. 7, the multi-mode linear-array transducer 704 may activate only a subset 654' of the transducer elements that were activated by the transducer 704 in the first imaging mode. At the same time, the ultrasound signals 110 projected from this subset 654' of transducer elements can be steered. For example, this may involve the transducer elements in the subset 654' being pulsed in a phased manner to generate a number of ultrasound signals 110 from the same portion of the transducer head 650'. In some embodiments, the steering of the ultrasound signals 110 may be in different directions so that a sector image 112 is generated.

During operation in the second mode, any remaining transducer elements 652' not in the subset remain inactive. This is so even if those transducer elements would normally be pulsed during the image acquisition process when a sequential linear-array transducer 104 (as shown in FIG. 1) is used in a conventional manner.

By providing a linear-array transducer 704 with a second mode of operation that activates only a subset 654' of the available transducer elements and simultaneously steers the ultrasound signals 110 generated from the subset 654' of transducer elements, the multi-mode linear-array transducer 704 may be able to simulate operation of a phased-array transducer that emits high-frequency ultrasound signals 110. This may allow the multi-mode linear-array transducer 704 to image volumes of tissue that would otherwise not be viewable using a conventional sequential linear-array transducer 104.

An example scenario where this may be desirable is when the tissue to be imaged is in the near field of the ultrasound image and it is desired take advantage of the high axial resolution offered by a conventional sequential linear-array transducer 104, but where there are structures obstructing travel of the ultrasound signals 110 near the surface of the skin. The available second mode of operation allows for imaging through available space where the ultrasound signals can 110 travel without requiring an ultrasound operator to switch transducer probes. For example, these scenarios may arise in certain pediatric applications where the tissue being imaged is not as deep. Some such pediatric applications include pediatric cardiac imaging that involves scanning the heart of children or babies through the space in between a child or baby's ribs. As with the multi-mode curvilinear-array transducer 606 shown in FIG. 6, use of the multi-mode linear-array transducer 704 may alleviate some drawbacks associated with having to switch transducer probes.

Shown generally as 701 in FIG. 7 are the image types 112, 114 that can be obtained using the multi-mode linear-array transducer 704. As shown, it can be seen that both the conventional rectangular image type 114 and a sector image type 112 can be obtained using a single multi-mode linear-array transducer 704. Referring again briefly to FIG. 1, this contrasts with the conventional one-to-one mapping between transducer types 102, 104, 106 and image types 112, 114, 116.

In conventional ultrasound systems, the footprint of a transducer probe selected to be used may generally depend on the physical constraints of the medical application. For example, the phased-array probe 102 may be used in situations where physically confined spaces on the patient's body does not allow for use of a transducer with a larger footprint. To the extent that the medical application allows for imaging with a transducer having a larger footprint that has a correspondingly larger number of transducer elements, it is generally desired to apply the sequential pulsing technique so as to obtain a larger field of view and avoid the degradation in far field lateral resolution.

However, in the present embodiments, despite the availability of additional transducer elements 652, 652' (as shown in FIGS. 6 and 7) that can be pulsed to generate an ultrasound image, the second mode of operation selectively activates only a particular subset 654, 654' of transducer elements and steers them to generate a sector image 112. By configuring a transducer with a larger number of transducer elements to operate in this manner, the multi-mode transducers 606, 704 may be able to perform additional imaging tasks. While the large footprint of the multi-mode transducers 606, 704 may prevent them from being used in all the same medical applications as a traditional phased-array transducer 102, the multi-mode transducers 606, 704 may still provide improved imaging functionality (and hence, versatility of examination) over traditional sequential linear-array transducers 104 and sequential curvilinear-array transducers 106.

As discussed above, the multi-mode curvilinear-array transducer 606 is configured to operate at relatively low frequencies, whereas the multi-mode linear-array transducer 704 is configured to operate at relatively high frequencies. However, these are only example configurations, and the methods and techniques described herein may be applicable to any type of transducer array that is configured to be activated in a sequential manner. For example, it may be possible to configure a multi-mode linear-array transducer 704 to operate at relatively low frequencies or a multi-mode curvilinear-array transducer 606 to operate at relatively high frequencies.

Referring to FIG. 8, shown there generally as 800 are the time delays and apertures used to perform beamforming when a multi-mode curvilinear-array transducer 606 (as shown in FIG. 6) is operated in the first imaging mode. As discussed above, the first imaging mode configures the multi-mode curvilinear-array transducer 606 to operate in manner similar to the conventional operation of a sequential curvilinear-array transducer 106 (as shown in FIGS. 1 and 2). As will be understood by persons skilled in the art, beamforming involves applying a time delay to when adjacent transducer elements 850 are pulsed so that the interference pattern generated by ultrasound signals 110 form a beam when projected. By varying the time delay and sequence in which the transducer elements 850 within a group are pulsed, the beam can be focused so that echo signals resulting from the beam are received as reflections from different tissue structures in a volume of interest.

FIG. 8 shows a simplified view of a transducer head 650 with its constituent transducer elements 850 and how they are pulsed at three example points in time during generation of an ultrasound image. As discussed above, to generate an ultrasound image in conventional operation of a sequential transducer, ultrasound beams are transmitted from different groups of adjacent transducer elements 850 sequentially and successively across the transducer head 650. These ultrasound beams result in the formation of scanlines that collectively generate the ultrasound image. The position of the transducer elements 850 on the transducer head 650 where the ultrasound signals get generated may be called the "aperture". As will be understood by persons skilled in the art, ultrasound operation may involve a transmit aperture and a receive aperture. The transmit aperture refers to the transducer elements 850 that are activated when the ultrasound signals 110 are generated, and the receive aperture refers to the transducer elements 850 that receive echo energy in response. The two apertures may be different such that they include different groups of transducer elements 850. Unless specifically indicated, the term "aperture" refers to the transmit aperture herein.

At the first point in time, the aperture 804A is on the leftmost portion of the transducer head 650 so that a group of adjacent transducer elements 850 there are pulsed. This group of adjacent transducer elements 850 are pulsed according to a time delay 802A. The time delay 802 is illustrated as an arc that represents the sequence of activation when the transducers elements 850 are pulsed. As shown, the outermost transducer elements 850 of the aperture 804A are pulsed first, and then transducer elements 850 towards the center of the aperture 804A are progressively pulsed. As will be understood by persons skilled in the art, this type of time delay 802A will generate an ultrasound beam 810A that focuses in a direction orthogonal to the surface of the transducer head 650.

At the second point in time, the aperture 804B is in the center portion of the transducer head 650. Since operation of the transducer in the first mode causes the ultrasound signal to be projected in a direction orthogonal to the surface of the transducer head 650, the same time delay 802A is applied to the aperture 804B to generate the ultrasound beam 810B.

At the third point in time, the aperture 804C is in the rightmost portion of the transducer head 650. A same time delay 802A is again applied to generate an ultrasound beam 810C that is perpendicular to the surface of the transducer head 650 at the position of the aperture 804C.

Referring to FIG. 9, shown there generally as 900 are the time delays and apertures used to perform beamforming when a multi-mode curvilinear-array transducer 606 (as shown in FIG. 6) is configured to perform imaging in the second imaging mode, in accordance with at least one embodiment of the present invention.

As discussed above, the second imaging mode configures the multi-mode curvilinear-array transducer 606 to only activate a subset 654 (as shown in FIG. 6) of the transducer elements 850 on the transducer head 650, but at the same time, steer the ultrasound signals 110 generated therefrom in multiple directions.

FIG. 9 shows a simplified view of a transducer head 650 with its constituent transducer elements 850 and how they are pulsed at three example points in time during generation of an ultrasound image during the second mode of operation.

At the first point in time, a time delay 802B is applied to an aperture 804D on the transducer head 650. Referring simultaneously to FIG. 8, it can be seen that the shape of the time delay 802B applied is different from the time delay 802A repeatedly applied in FIG. 8. The difference in time delay being applied to the aperture 804D causes the resultant ultrasound signal 910A to be steered in a direction that is different from just being orthogonal to the surface of the transducer head 650. Specifically, the particular time delay 802B shown has the rightmost transducer elements 850 within the aperture 804D being activated first and then progressively shifting to the left of the aperture 804D in the sequence and manner represented by the time delay 802B.

As will be understood by persons skilled in the art, the time delay 802B will cause the ultrasound signal 910A to be directed to the left.

At the second point in time, a time delay 802A is applied to the same aperture 804D that was activated during the first point in time. As can be seen, this time delay is different from the time delay 802B applied during the first point in time. Referring simultaneously to FIG. 8, it can be seen that the time delay 802A applied at the second point in time in FIG. 9 is substantially similar to the time delay 802A applied at various points in time in FIG. 8 to various apertures 804A, 804B, 804C. This is because at the second point in time in FIG. 9, the ultrasound signal 910B desired to be projected happens to be orthogonal to the surface of the transducer head 650.

At the third point in time, a time delay 802C is applied again to the same aperture 804D that was activated during the first and second points in time. The time delay 802C is different from the time delays 802B, 802A applied at the first and second points in time. As shown, the time delay 802C applied is in the reverse sequence and timing to the time delay 802B applied at the first point in time of FIG. 9. This results in the ultrasound signal 910C generated being directed to the right.

Referring simultaneously to FIGS. 8 and 9, it can be seen that when operating in the first mode (FIG. 8), the multi-mode curvilinear-array transducer 606 pulses different apertures 804A, 804B, 804C along the transducer head 650 with the same time delay 802A so as to cause ultrasound signals 810A, 810B 810C to be projected in respective directions that are orthogonal to the surface of the transducer head 650 at the locations of each aperture 804A, 804B, 804C. In contrast, in the second mode (FIG. 9), the multi-mode curvilinear-array transducer 606 repeatedly pulses a single aperture 804D on the transducer head 650 but with different time delays 802B, 802A, 802C to steer the respective ultrasound signals 910A, 910B, 910C in multiple directions.

Although FIGS. 8 and 9 have been shown and discussed with respect to the transducer head 650 of the multi-mode curvilinear-array transducer 606 originally shown in FIG. 6, the principles of aperture and delay configuration can be applied in a similar way to the multi-mode linear-array transducer 704 shown in FIG. 7 to provide the multiple imaging modes discussed herein. In other embodiments, the same principles may be applied to other types of ultrasound probes with transducer arrays that are conventionally activated in a sequential manner.

Figure 10:
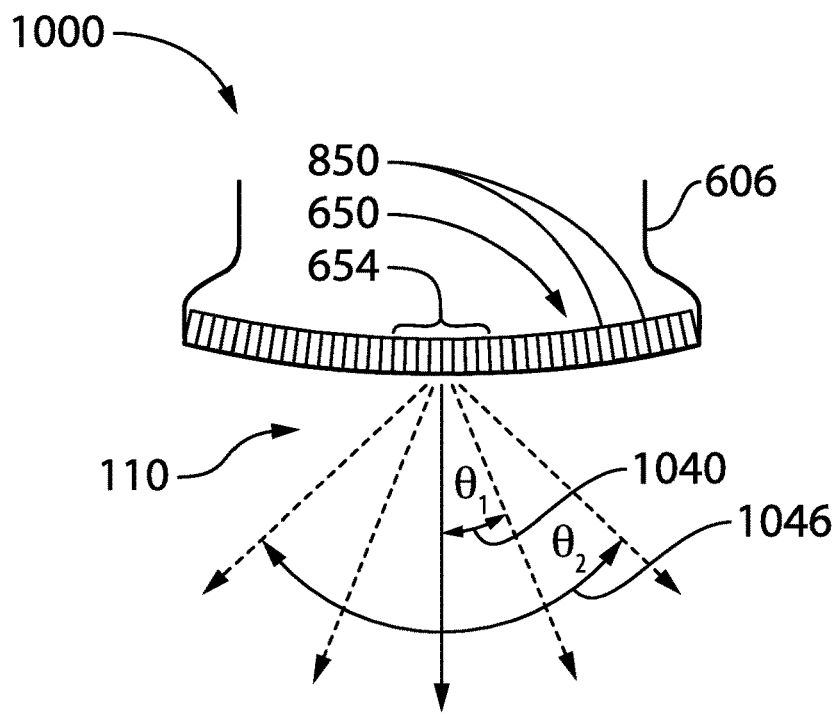
FIG. 10 shows an example configuration of the transducer elements provided on a multi-mode curvilinear-array transducer, in accordance with at least one embodiment of the present invention.

Referring to FIG. 10, shown there generally as 1000 is an example configuration of the transducer elements 850 provided on a multi-mode curvilinear-array transducer, in accordance with at least one embodiment of the present invention. As shown, the multi-mode curvilinear-array transducer 606 with the transducer head 650 includes its constituent transducer elements 850. When operated in the second mode, the subset 654 of the transducer elements 850 through which the ultrasound signals 110 are repeatedly transmitted can be made up of any number of transducer elements 850. In some embodiments, the transducer head 650 may be provided with at least 128 transducer elements 850 that can be activated during imaging in the first mode. For example, the subset 654 of these at least 128 transducer elements 850 that are activated during imaging in the second mode may include 16 to 96 of the at least 128 transducer elements. In a particular example embodiment, the transducer head may include 192 transducer elements, and the subset 654 of these 192 transducer elements may be any one of 16, 32, 64, 80, or 96 of the 192 transducer elements.

In some embodiments, when steering the ultrasound signals from the subset 654 of the transducer elements 850 that are activated in the second mode, the angular spacing 1040 between the respective different directions in which the ultrasound signals 110 are projected may be in the range of 0.35 to 0.70 degrees. In an example embodiment, the angular spacing 1040 may be 0.625 degrees.

As noted, the transducer elements 850 of the multi-mode curvilinear transducer 606 can be arranged along an arc having a radius of curvature. In various embodiments, the radius of curvature may be between 30 to 120 millimeters. In a particular example embodiment, the radius of curvature is 60 millimeters. As compared to a traditional phased-array transducer 102 that may have an aperture where the transducer elements 850 are arranged in a line, the time delays 802B, 802A, 802C (as shown in FIG. 9) that steer the ultrasound signals 110 in the second imaging mode may be adjusted to compensate for curvilinear arrangement of transducer elements 850. These adjustments may allow a traditional sector image 112 to be generated from a non-linear aperture 804D of transducer elements 850.

The construction of the array of transducer elements 850 may impact aspects of an ultrasound image. For example, certain configurations of the pitch (centre-to-centre distance between adjacent transducer elements 850) and cut width (the distance between adjacent transducer elements 850) may cause certain types of image artifacts to be more pronounced.

Referring simultaneously to FIG. 1, when traditional ultrasound transducer types 102, 104, 106 are designed, these various dimensions of the transducer element array may be configured to minimize the presence of image artifacts in a way that depends on the expected nature of their operation (e.g., sequential or phased, as discussed). For example, the transducer element array of a traditional phased-array transducer 102 may be configured to have a pitch of between 150-300 microns and a cut width of between 10-150 microns. Since the traditional phased-array transducer 102 is designed for acquiring signals by directing ultrasound signals 110 in multiple directions, configuring the transducer element array in this manner may allow for the ultrasound signals 110 to be steered in a broad range of directions without image artifacts (e.g., side lobe artifacts) appearing significantly in the resultant sector image 112. For example, such a configuration may allow a traditional sector image 112 to have a sector angle of approximately 90 degrees.

In comparison, the transducer element array of a traditional sequential curvilinear-array transducer 106 may be configured to have a pitch of between 200-400 microns and a cut width of between 10-200 microns. As compared to the traditional phased-array transducer 102, the differences in the dimensions of the transducer element array may allow for improved imaging when imaging in a sequential manner.

Referring back to FIG. 10, the transducer elements 850 of the multi-mode curvilinear transducer 606 in the present embodiments may be configured to have a pitch of between 100 to 400 microns and a cut width of between 10-200 microns. In a specific example embodiment, the pitch is 330 microns, and the cut width is 100 microns. This configuration for the transducer element array is more similar to that of a traditional sequential curvilinear-array transducer 106 than that of the traditional phased-array transducer 102, so as to allow for optimal imaging in the sequential manner of the first imaging mode.

However, such a configuration may not be as optimized for phased-array imaging as a traditional phased-array transducer 102. For example, in some embodiments, when imaging in the second mode, side lobe artifacts may appear more pronounced when ultrasound signals are steered in the leftmost and rightmost directions from the center line perpendicular to the surface of the aperture 804D (as shown in FIG. 9). This is compared to a traditional phased-array transducer 102, where the appearance of such side lobe artifacts may not be as pronounced. In some embodiments, to minimize the appearance of such side lobe artifacts, the sector angle 1046 of the sector image 112 may be reduced from the typical 90-degree sector angle produced by a traditional phased-array transducer 102. For example, the sector angle 1046 of the sector image 112 created by the multi-mode curvilinear-array transducer may be configured to be between 60-90 degrees, so that the sector image 112 does not display the outer edges of an image having the pronounced artifacts.

Figure 11:
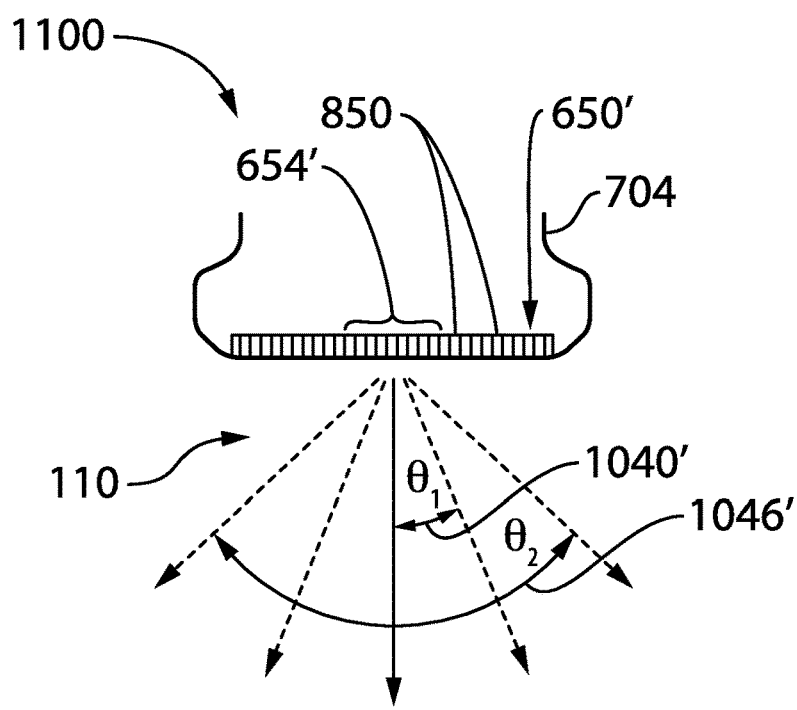
FIG. 11 shows an example configuration of the transducer elements provided on a multi-mode linear-array transducer, in accordance with at least one embodiment of the present invention.

Referring to FIG. 11, shown there generally as 1100 is an example configuration of the transducer elements 850 provided on a multi-mode linear-array transducer 704, in accordance with at least one embodiment of the present invention. Similar to the multi-mode curvilinear-array transducer 606, the multi-mode linear-array transducer 704 may be configured with a transducer head 650' including a number of transducer elements 850. A subset 654' of the transducer elements 850 may be activated during a second mode of operation. Again, similar to the multi-mode curvilinear-array transducer 606 discussed above, this subset 654' may be any number of the transducer elements 850 available on the transducer head 650'. The angular spacing 1040' between successive ultrasound signals 110 may also be similar to that of the multi-mode curvilinear-array transducer 606.

Referring simultaneously to FIG. 1, the transducer element array of a traditional sequential linear-array transducer 104 may have a pitch of between 100-300 microns and a cut width of between 10-150 microns. The multi-mode linear-array transducer 704 may be configured with a transducer element array having similar dimensions. Similar to the multi-mode curvilinear-array transducer 606 discussed above, in cases where there are differences between the configuration of the transducer element array in the multi-mode linear-array transducer 704 versus that which is in traditional phased-array transducer 102, there may be certain image artifacts that appear more pronounced on the outer edges of a sector image 112 generated using the second imaging mode of the multi-mode linear-array transducer 704. In some embodiments, the sector angle 1046' of the sector image 112 may also be configured to be less than 90 degrees (e.g., between 60-90 degrees) so that the sector image 112 does not display the outer edges of the image having the pronounced artifacts.

As noted above, for the multi-mode curvilinear-array transducer 606, the time delays 802B, 802A, 802C (as shown in FIG. 9) applied to steer the ultrasound signals 110 in the second imaging mode may be adjusted to compensate for the aperture 804D being positioned in a curve rather than a line. For the multi-mode linear-array transducer 704, these adjustments need not be applied because the transducer elements 805 are not positioned along a curve.

As shown in various figures herein, the subset 654, 654' of the transducer elements 850 that are activated during the second mode of imaging have been at or near the center portion of the transducer element array. However, in some alternate embodiments, the subset 654, 654' of transducer elements may be along any portion of the transducer element array. For example, in some embodiments, the subset 654, 654' of transducer elements 850 may be on the left edge or the right edge of the transducer element array. In some embodiments, the subset 654, 654' of the transducer elements 850 may be selected to be aligned with an external marking on the housing of the multi-mode transducers 606, 704 discussed herein.

Figure 12:
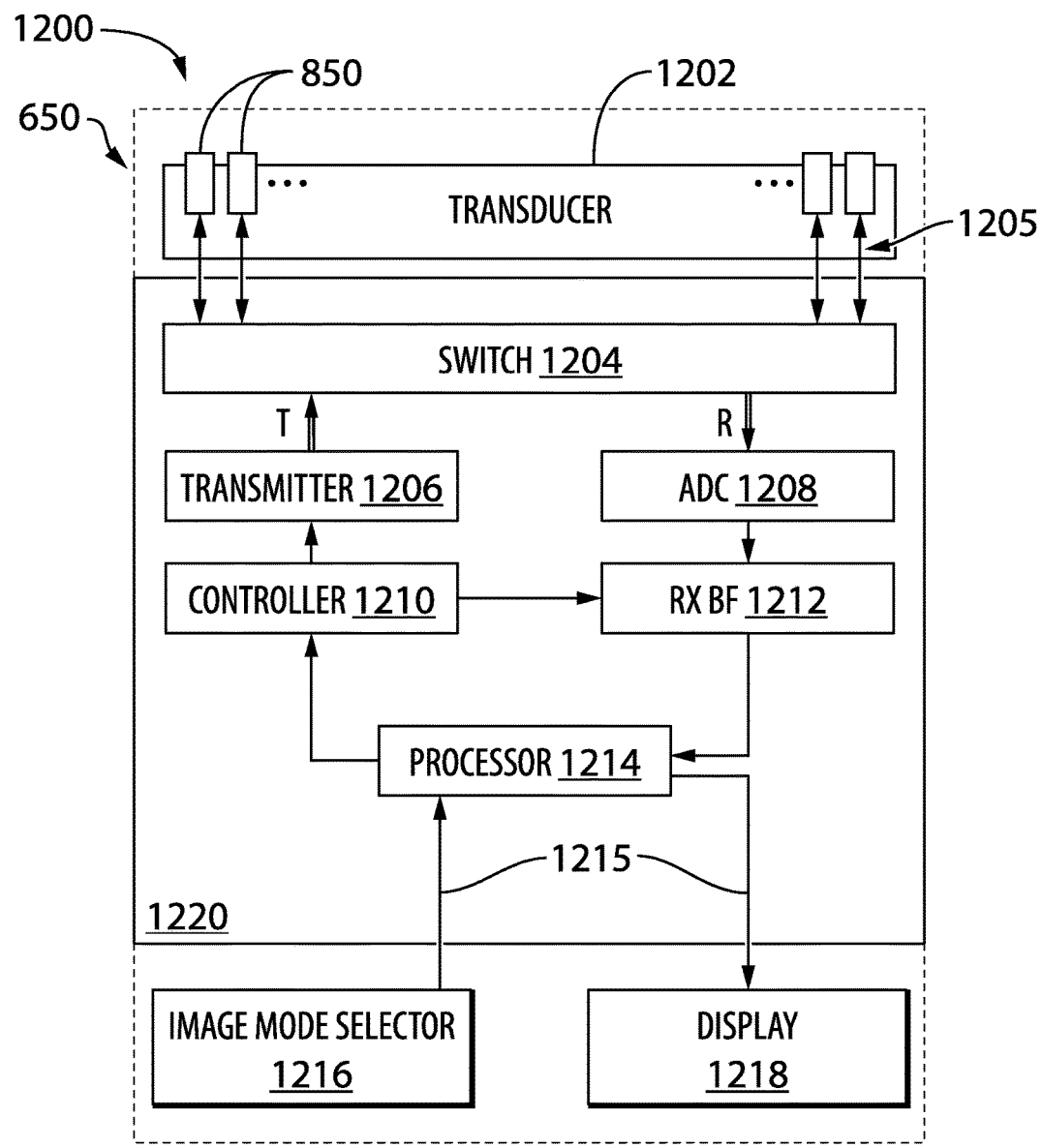
FIG. 12 shows a functional block diagram of an ultrasound machine, in accordance with at least one embodiment of the present invention.

Referring to FIG. 12, shown there generally as 1200 is a functional block diagram of an ultrasound machine, in accordance with at least one embodiment of the present invention. The ultrasound machine 1200 may include a transducer head 650 that may form part of the multi-mode curvilinear-array transducer 606 or the multi-mode linear-array transducer 704 discussed above. The transducer head 650 may include a transducer array 1202 with a number of constituent transducer elements 850.

A transmitter 1206 may be provided to energize the transducer elements 850 to produce the ultrasound signals 110. Another group of transducer elements 850 may then form the receive aperture to convert the received ultrasound energy into analog electrical signals which are then sent through a set of transmit/receive (T/R) switches 1204 to a number of channels of echo data. A set of analog-to-digital converters (ADCs) 1208 digitizes the analog signals from the switches 1204. The digitised signals are then sent to a receive beamformer 1212.

Transmitter 1206 and receive beamformer 1212 are operated under the control of a scan controller 1210. Receive beamformer 1212 combines the separate echo signals from each channel using pre-calculated time delay and weight values that may be stored in a coefficient memory (not shown) to yield a single echo signal which represents the received energy from a particular scanline. Under the direction of the scan controller 1210, the ultrasound machine 1200 generates and processes additional transmit and receive events to produce the multiple scanlines required to form an ultrasound image. Ultrasound images are typically made up of 50 to a few hundred lines. Typically, the number of scanlines of an ultrasound image generated from a sequential transducer may correspond to the number of transducer elements 850 in the transducer array 1202.

However, when the multi-mode array transducers 606, 704 described herein are operated in the second mode, the scanlines generated from the subset 654, 654' (as shown in FIGS. 6 and 7) of activated transducer elements 850 may not correlate to the number of the transducer elements 850 present in the transducer array 1202. Instead, the number of scanlines may correspond the configured angular separation 1040, 1040' of the transmitted ultrasound signals 110 that generate echo signals which form the sector image (as shown in FIGS. 10 and 11). In some embodiments, the apparatus and methods described herein may be employed using both Single Line Acquisition (SLA) and Multi-Line Acquisition (MLA) techniques. As will be understood by persons skilled in the art, images generated using SLA techniques have a single receive scanline for a single transmitted ultrasound signal 110 and images generated using MLA techniques have multiple receive scanlines for a single transmitted ultrasound signal 110. This may allow ultrasound systems that employ MLA techniques to have improved frame rates. In further embodiments, synthetic aperture techniques may be used in the first imaging mode and/or the second imaging mode to improve lateral resolution of an ultrasound image.

An ultrasound processor 1214 may be in communication with the receive beamformer 1212 and applies the necessary processing steps to combine multiple scanlines from these different transmit events to yield image data. The processor 1214 communicates this image data via a data link 1215 to a display device 1218. Data link 1215 may include a cable, a wireless connection, or the like. Display device 1218 displays the ultrasound image to the user. In some embodiments, the display device 1218 may not be separate, and instead be provided as an integrated part of the ultrasound machine 1200. In the latter case, the data link 1215 may be a data bus or other suitable connector between the processor 1214 and the display 1218.

The image mode selector 1216 may receive input to select between the first imaging mode and the second imaging mode discussed herein. The image mode selector 1216 may be provided in the form of any physical or software-based user interface control. For example, in some embodiments, a user control such as a push button, a graphical user interface control, or the like may be operated by an ultrasound operator. The data input selecting the mode of operation may be provided to ultrasound processor 1214 via data link 1215. In turn, the ultrasound processor 1214 may provide a configuration signal to controller 1210 to modify the operation of the transmitter 1206 and receive beamformer 1212 to activate the transducer array 1202 in accordance with the selected imaging mode.

The embodiments described herein may be used with ultrasound machines 1200 having a variety of different form factors. As illustrated in FIG. 12, the transducer head 650 is shown in dotted outline in relation to the processing components 1220 of the ultrasound machine 1200 to illustrate that it can be coupled thereto via any type of communication link 1205. For example, in some embodiments, the transducer may be detachably coupled to the body of the ultrasound machine 1200 via a cable or other suitable wired connection. In some such embodiments, the ultrasound machine 1200 may include both the processing components 1220 and the display 1218 and image mode selector 1216 in a unitary body.

In certain embodiments, the transducer head 650 and processing components 1220 may be provided in a single device (e.g., having a unitary body). In such case, the processor 1214 may communicate to display 1218 and image mode selector 1214 via a wireless communication link. The image mode selector 1216 and display 1218 is shown in dotted outline to show that they may not form part of the processing components 1220 in such embodiments. In some such embodiments, the single device containing the transducer head 650 and processing components 1220 may be provided as a wireless handheld probe that is configured to communicate with an external wireless computing device containing a display 1218 and is able to provide functionality for the image mode selector 1216. In some embodiments, such wireless handheld probe may be provided in a form factor that has a mass that is less than 4.5 kilograms.

Configuring a single transducer head 650 to operate in multiple imaging modes as described herein may be desirable in embodiments where the transducer head 650 and the processing components 1220 are provided in a unitary body because it is not possible to remove the transducer head 650 from the body containing the processing components 1220. Put another way, configuring the single, non-detachable transducer head 650 to operate in multiple imaging modes may provide enhanced utility of a wireless handheld ultrasound probe.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An ultrasound imaging method comprising, by an ultrasound imaging machine:
    imaging in a first mode using a sequential transducer comprising a plurality of transducer elements, wherein when imaging in the first mode, groups of adjacent transducer elements of the plurality of transducer elements are sequentially pulsed for beamforming, and the groups of adjacent transducer elements correspond to respective different apertures along a head of the sequential transducer; and
    imaging in a second mode different from the first mode, wherein when imaging in the second mode, a subset of at least two of the plurality of transducer elements form a single aperture on the head of the sequential transducer, and the subset of transducer elements are repeatedly pulsed with different phase shifts for beamforming through the single aperture so that a plurality of ultrasound signals are steered from the subset of the plurality of transducer elements, and wherein any remaining transducer elements of the plurality of transducer elements not part of the subset are inactive when imaging in the second mode.

2. The ultrasound imaging method of claim 1, wherein
the beamforming performed when imaging in the first mode comprises delayed activation of the transducer elements within each of the groups of adjacent transducer elements, and a same time delay is used for all the groups of adjacent transducer elements corresponding to the respective different apertures along the head of the sequential transducer; and
the beamforming performed when imaging in the second mode comprises delayed activation of the transducer elements within the subset of transducer elements, and the beamforming is repeatedly performed on the subset of transducer elements using a plurality of different time delays to steer the plurality of ultrasound signals from the single aperture on the head of the sequential transducer.

3. The ultrasound imaging method of claim 1, wherein when imaging in the second mode, each of the plurality of ultrasound signals is steered in a respective different direction so that a sector image is generated.

4. The ultrasound imaging method of claim 3, wherein the sector image has a sector angle of 60 to 90 degrees.

5. The ultrasound imaging method of claim 3, wherein angular spacing between the respective different directions is between 0.35 to 0.70 degrees.

6. The ultrasound imaging method of claim 1, wherein the sequential transducer comprises a curvilinear-array transducer, and the plurality of transducer elements are arranged along an arc having a radius of curvature of between 30 to 120 millimeters.

7. The ultrasound imaging method of claim 1, wherein the plurality of transducer elements comprise a pitch spacing between each adjacent transducer element, and the pitch spacing is between 100 to 400 microns.

8. The ultrasound imaging method of claim 1, wherein the plurality of transducer elements comprises at least 128 transducer elements and the subset of the plurality of transducer elements comprises 16 to 96 of the at least 128 transducer elements.

9. An ultrasound imaging machine, comprising:
an ultrasound processor; and
a sequential transducer communicably coupled to the ultrasound processor, the sequential transducer comprising a plurality of transducer elements;
wherein the ultrasound imaging machine is:
operable in a first imaging mode in which the ultrasound processor sequentially pulses groups of adjacent transducer elements of the plurality of transducer elements for beamforming, and the groups of adjacent transducer elements correspond to respective different apertures along a head of the sequential transducer; and
operable in a second imaging mode different from the first imaging mode, and in the second imaging mode, the ultrasound processor pulses a subset of at least two of the plurality of transducer elements that form a single aperture on the head of the sequential transducer, wherein the subset of transducer elements are repeatedly pulsed with different phase shifts for beamforming through the single aperture so that a plurality of ultrasound signals are steered from the subset of the plurality of transducer elements, and wherein any remaining transducer elements of the plurality of transducer elements not part of the subset are inactive when operating in the second imaging mode.

10. The ultrasound imaging machine of claim 9, wherein
the beamforming performed when in the first imaging mode comprises delayed activation of the transducer elements within each of the groups of adjacent transducer elements, and a same time delay is used for all the groups of adjacent transducer elements corresponding to the respective different apertures along the head of the sequential transducer; and
the beamforming performed when in the second imaging mode comprises delayed activation of the transducer elements within the subset of transducer elements, and the beamforming is repeatedly performed on the subset of transducer elements using a plurality of different time delays to steer the plurality of ultrasound signals from the single aperture on the head of the sequential transducer.

11. The ultrasound imaging machine of claim 9, wherein each of the plurality of ultrasound signals is steered in a respective different direction, so that a sector image is generated.

12. The ultrasound imaging machine of claim 11, wherein the sector image has a sector angle of 60 to 90 degrees.

13. The ultrasound imaging machine of claim 11, wherein angular spacing between the respective different directions is between 0.35 to 0.70 degrees.

14. The ultrasound imaging machine of claim 9, wherein the sequential transducer comprises a curvilinear transducer, and the plurality of transducer elements are arranged along an arc having a radius of curvature of between 30 to 120 millimeters.

15. The ultrasound imaging machine of claim 9, wherein the plurality of transducer elements comprise a pitch spacing between each adjacent transducer element, and the pitch spacing is between 100 to 400 microns.

16. The ultrasound imaging machine of claim 9, wherein the plurality of transducer elements comprises at least 128 transducer elements and the subset of the plurality of transducer elements comprises 16 to 96 of the at least 128 transducer elements.

17. The ultrasound imaging machine of claim 9, wherein the sequential transducer comprises a housing containing the plurality of transducer elements, and the housing comprises a marking indicating a position of the subset of the plurality of transducer elements amongst the plurality of transducer elements.

18. A sequential ultrasound transducer, capable of being communicably coupled to an ultrasound processor, the sequential ultrasound transducer comprising:
a plurality of transducer elements, wherein when the sequential ultrasound transducer is communicably coupled to the ultrasound processor, the ultrasound processor is configured to:
activate the plurality of transducer elements in a first imaging mode, wherein in the first imaging mode, groups of adjacent transducer elements of the plurality of transducer elements are sequentially pulsed for beamforming, and the groups of adjacent transducer elements correspond to respective different apertures along a head of the sequential transducer; and activate a subset of at least two of the plurality of transducer elements in a second imaging mode that is different from the first imaging mode, wherein in the second imaging mode, the subset forms a single aperture on the head of the sequential transducer, and the subset of transducer elements are repeatedly pulsed with different phase shifts for beamforming through the single aperture so that a plurality of ultrasound signals are steered from the subset of the plurality of transducer elements, and wherein any remaining transducer elements of the plurality of transducer elements not part of the subset are inactive, when in the second imaging mode.

\* \* \* \* \*